United States Patent [19]
Byrd

[11] Patent Number: 5,228,448
[45] Date of Patent: Jul. 20, 1993

[54] PROTECTIVE COVER FOR BLOOD-PRESSURE CUFFS

[76] Inventor: Timothy N. Byrd, 1267 Old Cades Cove Rd., Townsend, Tenn. 37882

[21] Appl. No.: 753,939

[22] Filed: Sep. 3, 1991

[51] Int. Cl.$^5$ .......................................... A61B 5/022
[52] U.S. Cl. .................................. 128/677; 128/686; 128/672; 128/855; 206/303
[58] Field of Search ............... 128/384, 855, 881, 672, 128/677, 686; 2/60; 206/303; 606/202, 203, 201, 204

[56] References Cited

U.S. PATENT DOCUMENTS

| | | |
|---|---|---|
| 2,244,871 | 6/1941 | Guinzburg . |
| 3,473,525 | 10/1969 | Hanafin . |
| 4,197,944 | 4/1980 | Catlin . |
| 4,334,611 | 6/1982 | Watson et al. ........................ 206/303 |
| 4,378,009 | 3/1983 | Rowley et al. .................. 606/202 X |
| 4,548,249 | 10/1985 | Slaughterbeck . |
| 4,549,550 | 10/1985 | Kami .............................. 128/686 |
| 4,572,173 | 2/1986 | Comeau . |
| 4,905,715 | 3/1990 | Johnson ............................ 602/23 X |
| 4,911,151 | 3/1990 | Rankin et al. ...................... 128/82 |

FOREIGN PATENT DOCUMENTS 15450  8/1888  United Kingdom ..................... 2/60

OTHER PUBLICATIONS

From Journal Anesthesia Analgesia; Andrew L. Stemlicht Alan Van Poznak, M.D.; "Significant Bacterial Colonization Occurs On The Surface of Non-Disposable Sphygmomanometer Cuffs and Re-Used Disposable Cuffs"; 1990.

*Primary Examiner*—Randall Green
*Assistant Examiner*—D. Willse
*Attorney, Agent, or Firm*—Griffin, Butler, Whisenhunt & Kurtossy

[57] ABSTRACT

A protective cover (16) for covering a blood-pressure cuff (10) comprises a flexible sheet defining an elongated bottom band (24), an elongated top band (30), and an intermediate portion (38) interconnecting the bottom and top bands. The bottom and top bands have widths which are substantially greater than a width of the blood-pressure cuff. A length of the bottom band is greater than a distance about an appendage (14) about which the blood-pressure cuff is to be wrapped and a length of the top band is greater than a distance about an outer surface of the blood-pressure cuff when it is wrapped about the appendage. The sheet is two-ply, having an exterior layer (18) of soft absorbent material and an interior layer (20) of more liquid impervious material. The bottom band is wrapped about the appendage, the blood-pressure cuff is wrapped about the bottom portion, and the top band is pivoted relative to the bottom band at the intermediate portion over the blood-pressure cuff and wrapped thereabout.

3 Claims, 2 Drawing Sheets

PROTECTIVE COVER FOR BLOOD-PRESSURE CUFFS

BACKGROUND OF THE INVENTION

This invention relates generally to blood-pressure cuffs of sphygmomanometers and more particularly to devices which can be used to prevent such cuffs from becoming contaminated and/or from contaminating patients.

Studies have shown that significant bacterial colonizations occurs on surfaces of non-disposable sphygmomanometer cuffs as well as on reused disposable cuffs. Such studies have indicated that medical staffs employing such cuffs, including nursing professionals, almost never routinely clean them between patients and few regard such cuffs as being possible sources of infection. Only clean, non-used, disposable cuffs were shown to have insignificant colonization rates during one such study. Thus, it has been recommended that, where possible, a sterilized cuff, or an unused disposable cuff, be dedicated to each patient upon arrival at a hospital and that the cuff follow the patient around in the hospital. A difficulty with this solution is that it is an administrative problem to maintain a cuff in association with each patient. Also, if a blood-pressure cuff is dedicated to each patient, an unduly large number of cuffs is required, which is expensive. Although disposable cuffs exist, their use is also expensive. Further, the acquisition, storage, and handling of large numbers of cuffs is difficult and not cost effective. Thus, it is an object of this invention to provide a means for preventing blood-pressure cuffs from becoming contaminated and from spreading contamination in an uncomplicated and cost effective manner without employing relatively large numbers of disposable and/or non-disposable blood-pressure cuffs and without maintaining associations between particular patients and cuffs.

U.S. Pat. No. 4,548,249 to Slaughterbeck suggests the use of replaceable protective sleeves for sphygmomanometer cuffs. A protective sleeve described in that patent is somewhat enveloped shaped, being closed at both ends but open at a side edge for receiving a blood-pressure cuff therein. A problem with the protective sleeve of this patent is that it does not have universal application, being useful only with particularly configured blood-pressure cuffs. Also, when a blood-pressure cuff is inserted in such a sleeve, attaching devices of the cuff, which hold it about a patient's appendage during use, are initially covered. Therefore, provision must be made for uncovering these attaching devices. Thus, the protective sleeve of that patient is provided with removable windows, which add expense to the protective sleeve. Further, when the attaching devices thereof are uncovered in this manner, they can become contaminated and can pass on such contamination. Thus, it is an object of this invention to provide a protective cover for a blood-pressure cuff which must not be custom formed to a particular blood-pressure cuff, which does not uncover portions of the cuff during use, and which is inexpensive to construct.

It is a further object of this invention to provide a protective cover for a blood-pressure cuff which does not affect the accuracy of a sphygmomanometer of which the cuff is part, which is not uncomfortable for a patient to use, which is not inconvenient or time consuming for medical personnel to use, but yet which provides a wide margin of security from contamination for both patients and medical personnel.

SUMMARY

According to principles of this invention, a protective cover for blood-pressure cuffs comprises a basically single-plane flexible sheet having bottom and top portions in the shape of elongated, substantially-parallel, bottom and top bands and an intermediate portion interconnecting the bottom and top bands along lengths thereof. The bottom and top bands of the respective bottom and top portions have widths which are substantially greater than a width of a blood-pressure cuff to be thereby covered, the bottom band having a length which is greater than a distance about an appendage on which the blood-pressure cuff is used and the top band having a length which is greater than a distance about an outer surface of the blood-pressure cuff when it is wrapped about the appendage. The intermediate portion has a length which is substantially less than the distance about the appendage. In use, the bottom band is wrapped about the appendage, the blood-pressure cuff is wrapped about the bottom band, the top band is pivoted relative to the bottom band at the intermediate portion over the blood-pressure cuff and then wrapped about the blood-pressure cuff to cover it.

The flexible sheet, in a preferred embodiment, is fluid impervious but, also in a preferred embodiment, it is a two-ply sheet with an exterior layer, facing the appendage and away from the blood-pressure cuff, being of a soft absorbent material and an interior layer, facing the cuff, being of a more liquid impervious material. In a preferred embodiment, the bottom band of the bottom portion is shorter than the top band of the top portion.

The bottom band includes an attachment device for attaching opposite end portions of the bottom band together when the bottom band is wrapped about the appendage and the top band includes an attachment device for attaching opposite end portions of the top band together when it is wrapped about the blood-pressure cuff. The attachment devices can include adhesives.

BRIEF DESCRIPTION OF THE DRAWING

The foregoing and other objects, features and advantages of the invention will be apparent from the following more particular description of a preferred embodiment of the invention, as illustrated in the accompanying drawings in which reference characters refer to the same parts throughout the drawings. The drawings are not necessarily to scale, emphasis instead being placed upon illustrating principles of the invention in a clear manner.

DESCRIPTION OF A PREERRED EMBODIMENT

Figure 1:
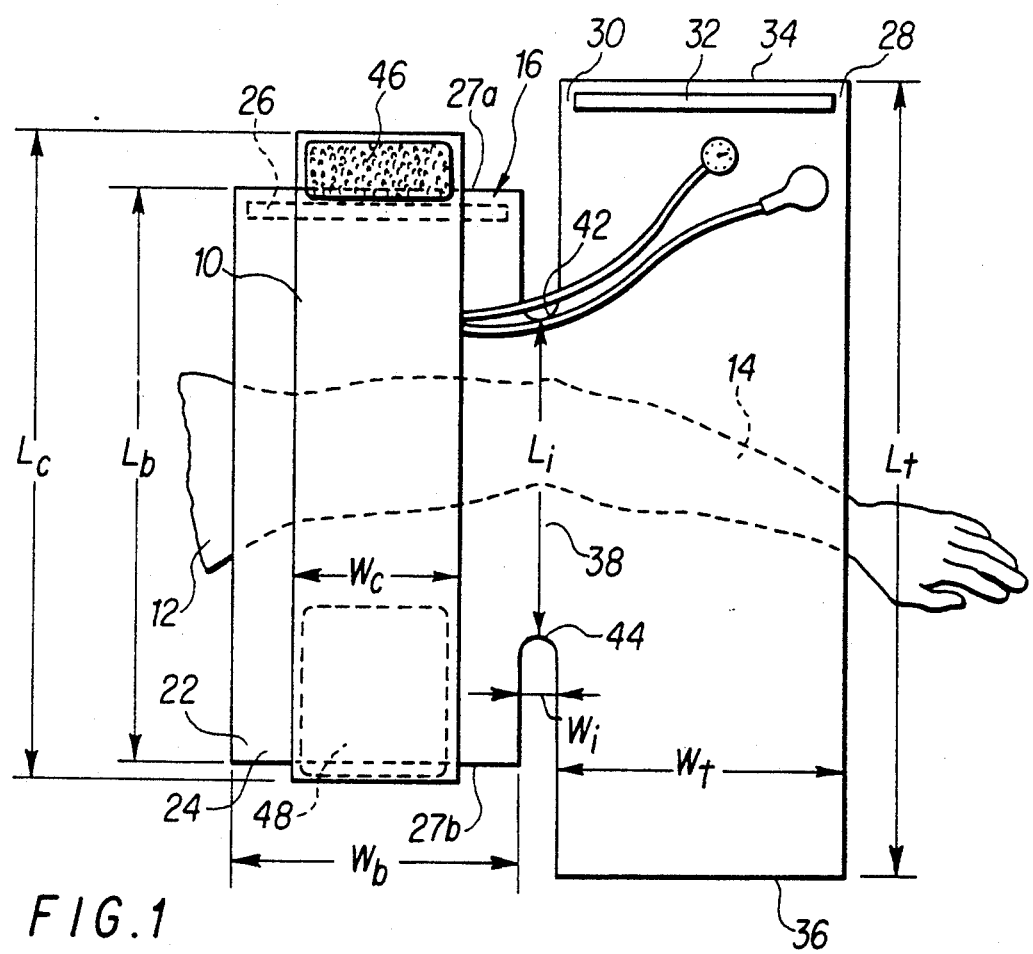
FIG. 1 is a top plan view of a protective cover of this invention extended in a flat plane above an arm with a blood-pressure cuff being positioned above a bottom portion of the protective cover.

FIG. 1 depicts an inflatable blood-pressure cuff 10 of a sphygmomanometer for measuring the blood pressure of a patient 12 by wrapping the blood-pressure cuff 10 about an appendage 14 of the patient's body. In this case, as is normal, the appendage 14 is the patient's arm. Also shown in FIG. 1 is a protective cover 16 of this invention to be used in conjunction with the blood-pressure cuff 10 for taking the blood pressure measurement. Although the blood-pressure cuff 10 and the protective cover 16 are shown extended in planes, with the blood-pressure cuff 10 being above the protective cover 16, both of these elements are quite flexible and will normally not be in such configurations one positioned above the other as shown in FIG. 1.

The protective cover 16 is basically a flexible sheet which will normally include a liquid impervious layer. In this regard, in a preferred embodiment, the protective cover 16 is a two-ply sheet, having an exterior layer 18 of a soft, absorbent material and a thin interior layer 20 of a relatively soft, flexible, plastic film, which is basically liquid impervious. Such a two-ply sheet is currently being sold by Erving Paper Mills as "polyback tissue", a name used in the trade for such material. It can be seen in FIG. 2 that the exterior layer 18 lies against a surface of the patient's appendage 14 to provide comfort for the patient 12 while the liquid impervious interior layer 20 faces the blood-pressure cuff 10 so as to protect the blood-pressure cuff 10 from outside contamination and to prevent contamination from spreading outwardly from the blood-pressure cuff 10.

Figure 2:
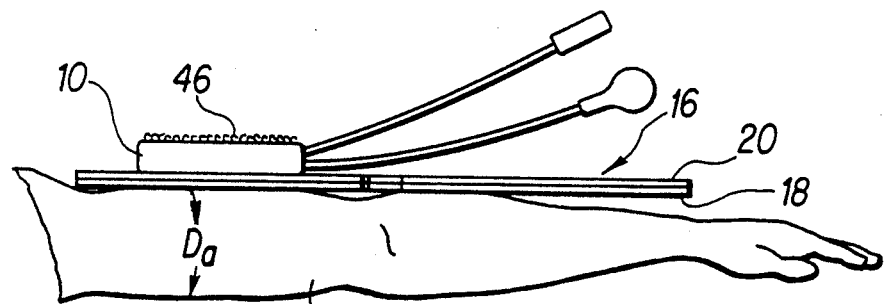
FIG. 2 is a side elevational view of the structure of FIG. 1.
Figure 3:
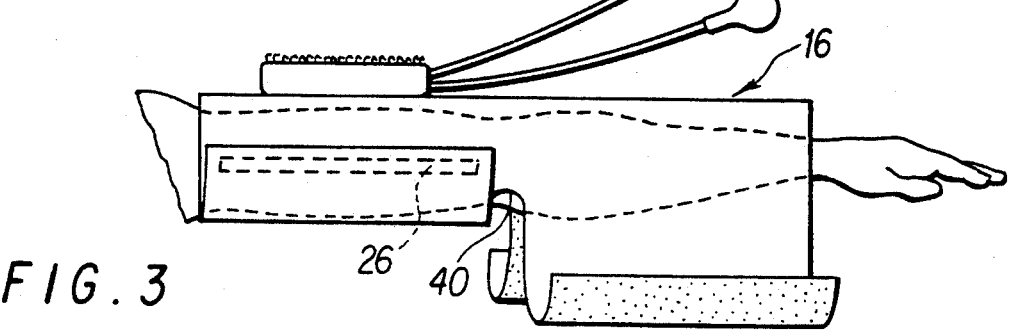
FIG. 3 is a view similar to FIG. 2, but with a bottom band of the bottom portion of the protective cover being wrapped about the arm.

The protective cover 16 is shaped to have a bottom portion 22 in the shape of an elongated bottom band 24. The length of the bottom band 24, $L_b$, in one embodiment, is approximately 18 inches, while its width $W_b$ is approximately nine inches. The length $L_b$ must be sufficiently great that the lower band 24 can be completely wrapped about the appendage 14 with its ends substantially overlapping. That is, $L_b > D_a$ where $D_a$ is the complete distance about the arm 14 as illustrated in FIG. 2. The width $W_b$ of the bottom band 24 must be substantially greater than a width $W_c$ of the blood-pressure cuff 10, as can be seen in FIG. 1. In this regard, the width of blood-pressure cuffs vary, however, they are usually in a range of 2½ inches to 6⅜ inches which is substantially less than the nine inch width $W_b$ of the bottom band 24. Thus, in this embodiment, the width $W_b$ of the bottom band 24 is at least 2⅜ inches wider than the width of the blood-pressure cuff (9 inches−6⅜ inches=2⅜ inches) and a minimum width therefor would therefore be around 4⅞ inches (2½ inches+2⅜ =4⅞ inches) to provide a desired margin for the smallest blood-pressure cuffs. The bottom band 24 of the depicted embodiment has a uniform width along its length; however, this is not essential so long as this band is shaped to form a band completely about the appendage 14 which is substantially wider than the width of the blood-pressure cuff. The bottom band 24 includes an attachment device 26 near one of its opposite ends 27a and 27b for attachment to a portion of the other opposite end so that ends of the bottom band 24 can be attached together to retain the bottom band 24 wrapped about the appendage 14, as it is depicted in FIG. 3. In a preferred embodiment, the attachment device 26 is a pressure sensitive adhesive strip, which is relatively inexpensive, however, it can be formed of other materials as well.

Figure 4:
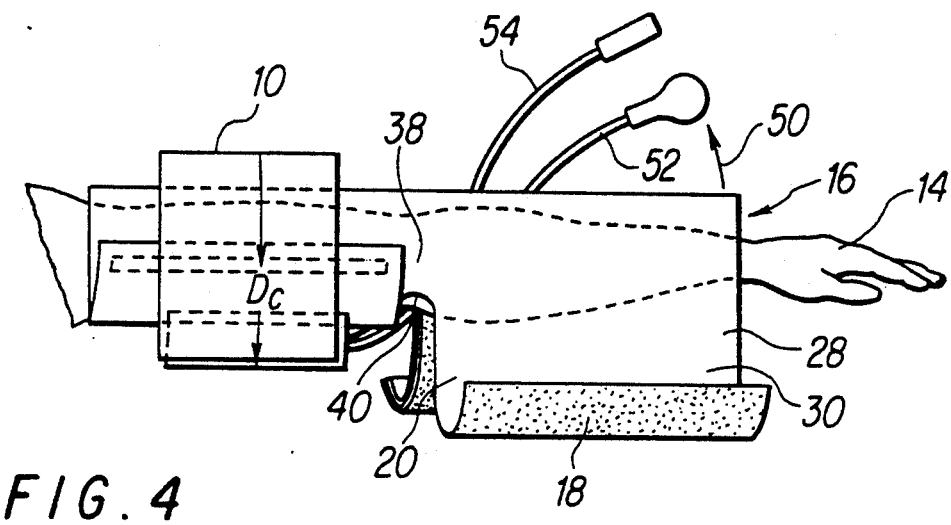
FIG. 4 is a view similar to FIG. 3 but with the blood-pressure cuff being wrapped about the bottom portion of the protective cover and the arm protective cover.
Figure 5:
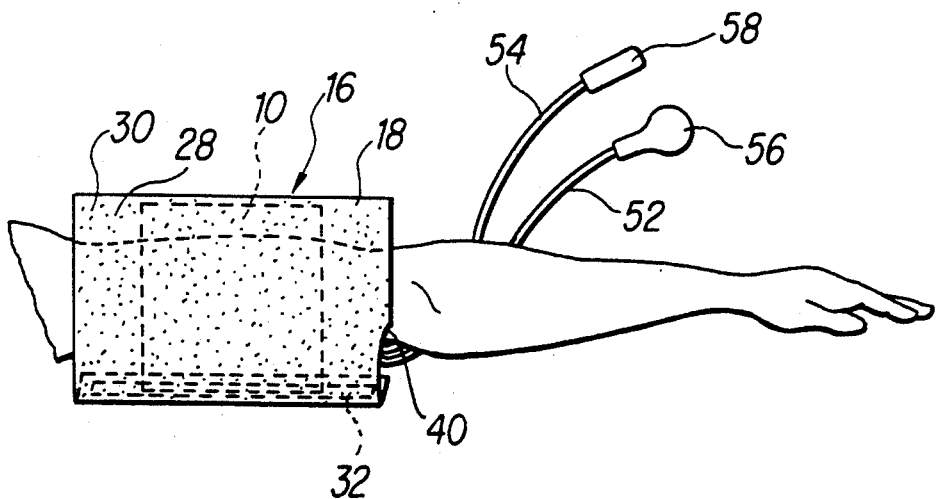
FIG. 5 is a view similar to FIG. 4 but with a top portion of the protective cover being rotated at an intermediate portion of the protective cover over the blood-pressure cuff and wrapped about the cuff, the arm, and the first portion of the blood-pressure cuff.

The protective cover 16 also includes a top portion 28 having a shape of a top band 30. The top band 30, in a preferred embodiment, has a width $W_t$ of about nine inches and a length $L_t$ of about 25 inches, which is longer than the length $L_b$ of the bottom band 24. In this regard, these exact dimensions are not critical, however, it is important that the width $W_t$ of the top band 30 be substantially greater than the width $W_c$ of the blood-pressure cuff 10 and that its length $L_t$ be greater than a distance $D_c$ (FIG. 4) completely about the blood-pressure cuff 10 when it is wrapped about the appendage 14, as shown in FIG. 4. Again, the top band 30 is shown as having a uniform width along its length. This is not critical although the top band 30, when its ends are wrapped about the blood-pressure cuff 10 as shown in FIG. 5, must form a circular band for completely covering the blood-pressure cuff 10. The top portion 28 also includes an adhesive attachment device 32 for interconnecting opposite end portions 34 and 36 of the top band 30.

The protective cover 16 also includes an intermediate, or hinge, portion 38 for interconnecting the bottom band 4 and the top band 30 along their lengths. The length $L_i$ of the intermediate portion 38 is substantially less than the distance $D_a$ about the appendage 14, as shown in FIG. 2, so that when the bottom band 24 is wrapped about the appendage 14, as depicted in FIG. 3, a substantial space 40 remains between ends 42 and 44 of the intermediate portion 38. A width $W_i$ of the intermediate portion 38, in a preferred embodiment, is about an inch and a half, which is the approximate thickness of the blood-pressure cuff 10 when it is wrapped and inflated. This ensures an accurate reading with the cuff by not causing false pressure on a bladder of the cuff.

In a method of using the protective cover of this invention, when blood pressure is to be taken by wrapping the blood-pressure cuff 10 about the appendage 14, the protective cover is placed adjacent the appendage as is depicted in FIG. 1 and the bottom band 24 is wrapped about the appendage as is depicted in FIG. 3. The ends 27a and 27b of the bottom band 24 are attached together by means of the attachment device 26 so that the band is held in this wrapped configuration. The blood cuff 10 is then placed adjacent to, and centered on, the bottom band 24, as is depicted in FIG. 3, and wrapped thereabout as is depicted in FIG. 4. The blood-pressure cuff 10 is held in this wrapped configuration by its attaching devices 46 an 48 which are on surfaces of the blood-pressure cuff 10. It should be noted that in this configuration side edges of the blood pressure cuff are substantially inwardly spaced from side edges of the bottom band. The next step in the procedure is to pivot the top band 30, as shown by arrow 50 in FIG. 4, at the intermediate portion 38 so that the plastic, liquid-impervious, interior, layer 20 of the top band 30 faces the wrapped blood-pressure cuff 10 and the softer, absorbent, exterior, layer 18 faces away from the blood-pressure cuff 10. In this configuration, as can be seen in FIG. 5, the space 40 left between ends 42 and 44 of the intermediate portion 38 allows sphygmomanometer tubes 52 and 54 to communicate with their respective pump 56 and gauge 58. The top band 30 is held in this configuration by the attachment device 32 which interconnects ends of the top band 30.

As can be seen in FIG. 5, the top band 30 forms a band about the appendage and the blood pressure cuff which is substantially wider than the width of the blood-pressure cuff, with side edges thereof extending beyond side edges of the blood pressure cuff. The blood-pressure cuff 10 is then inflated via the pump tube 52, and after a blood pressure reading is taken, it is deflated in a similar manner. The top band 30 is detached and rotated away from the blood-pressure cuff 10 at the intermediate portion 38, the blood pressure cuff 10 is detached and removed, and the bottom band 24 is detached and removed. The protective cover 16 is then discarded and a new one is used with the next reading taken with the same blood pressure cuff.

It will be appreciated by those of ordinary skill in the art that the protective cover 16 of this invention, being mainly a flat flexible sheet, is extremely inexpensive and uncomplicated to construct. Further, since the protective cover 16 is constructed as a two-ply sheet, it can include a soft absorbent layer for contacting a patient's appendage and facing outwardly, to be touched by outsiders. This soft, absorbent layer also tends to absorb and contain superfluous fluids which could spread and thereby contaminate the blood-pressure cuff 10, and/or personnel. This two-ply construction also allows the interior layer 20 to be impervious to liquids so that liquids cannot communicate between a patient and the blood-pressure cuff 10.

Yet another benefit of this invention comes from the fact that the bottom and top bands 24 and 30 are wider than the blood-pressure cuff 10 by a substantially great margin so that security is provided to patients and surgical personnel that the blood-pressure cuff is adequately covered and therefore will not receive or transmit contamination.

Still another benefit of this invention is that its shape, which creates the space 40, directs tubes passing through the space 40 away from the body of a patient and thereby keeps the tubes from becoming contaminated by body wounds. This also prevents a body wound from being contaminated by the tubes.

Because of the unusual shape of the protective cover 16, surgical personnel can quickly apply the bottom portion to an appendage, can quickly apply a blood-pressure cuff to the bottom portion, and can quickly fold the top portion over the blood-pressure cuff with very little difficulty. In this regard, it is not necessary to carefully thread the blood-pressure cuff 10 into a sleeve or the like. However, this unusual shape is not difficult to construct, being basically stamped out of off-the-shelf sheet material, so that a protective cover of this invention can be inexpensively and easily constructed.

Also, the soft, absorbent exterior layer 18 of the protective cover, being against the patient's skin, makes it relatively comfortable for a patient. Because the protective cover 16 is extremely thin, it does not significantly affect accuracy of a sphygmomanometer reading taken as described herein.

By making the length of the bottom band 24 less than the length of the top band 30, material and bulk are saved. In this regard, protective covers 16 of this invention are relatively easy to transport, store, maintain, and distribute.

It should be understood that the protective covers 16 of this invention are disposable. If a blood-pressure cuff is not removed from an arm, the protective cover of this invention may be used for several readings. Usually, however, it will be disposed of after each use. Although after a blood pressure measurement has been made a protective cover used therewith is usually thrown away, the blood-pressure cuff 10 which was used therewith need not be thrown away or even carefully cleaned because it was protected from contamination by the protective cover 16 during the measurement and because, even if it became contaminated, again, a new protective cover 16 will prevent it from spreading this contamination.

Adhesives for the attachment devices 26 and 32 are relatively inexpensive and easy to use.

While the invention has been particularly shown and described with reference to a preferred embodiment, it will be understood by those skilled in the art that various changes in form and detail may be made therein without departing from the spirit and scope of the invention. In this regard, for example, the flexible sheet material of which the protective cover is made could be a single-ply, impervious or non-impervious, inexpensive material. Also, the intermediate portion 38 need not have any width $W_1$ whatsoever, although by having a width $W_1$ the protective cover introduces less restriction on a pressure gage bladder and thereby leads to greater accuracy. Also, this member need have very little length $L_i$, although by having some length, as depicted herein, it aids in properly positioning the bottom and top bands relative to one another and in creating a space 40 for controlling attitudes of pressure gage tubes.

The embodiments of the invention in which an exclusive property or privilege are claimed or defined as follows:

1. A method of applying a blood-pressure cuff and a protective flexible-sheet cover for covering the blood-pressure cuff to an appendage, said method comprising the steps of:
   wrapping a bottom portion of said protective cover about the appendage, said bottom portion forming a band completely about said appendage which is wider than a width of said blood-pressure cuff;
   wrapping said blood-pressure cuff about said bottom portion, with side edges of said blood-pressure cuff being substantially inwardly spaced from side edges of said bottom portion;
   pivoting a top portion of said protective cover over said blood-pressure cuff at an intermediate portion of said protective cover and wrapping said top portion about said appendage and said wrapped blood-pressure cuff, said top portion forming a band about said appendage and said blood-pressure cuff which is substantially wider than the width of said blood-pressure cuff with side edges thereof extending beyond side edges of said blood-pressure cuff.

2. A method as in claim 1 wherein said intermediate portion has a length which is substantially less than the lengths of either said bottom or top bands.

3. A method as in claim 2 wherein said intermediate portion has a length which is substantially less than a distance about the appendage.

* * * * *